(12) United States Patent
Diehl et al.

(10) Patent No.: US 6,588,421 B1
(45) Date of Patent: Jul. 8, 2003

(54) HME BYPASS SYSTEM

(75) Inventors: Stephen David Diehl, Waterville, NY (US); Edgar Delgado, Triadelphia, WV (US); Bernard Wesley Baker, Jr., Herkimer, NY (US)

(73) Assignee: DHD Healthcare Corporation, Wampsville, NY (US)

( * ) Notice: Subject to any disclaimer, the term of this patent is extended or adjusted under 35 U.S.C. 154(b) by 188 days.

(21) Appl. No.: 09/677,020

(22) Filed: Sep. 29, 2000

(51) Int. Cl.[7] ............................................... A62B 18/08
(52) U.S. Cl. ........................ 128/201.13; 128/204.17; 128/912; 128/205.24; 165/130
(58) Field of Search ................ 128/201.13, 204.17, 128/909, 911, 912, 205.24, 203.26, 203.22; 165/119, DIG. 37, DIG. 40, DIG. 41, DIG. 109, DIG. 110, DIG. 113, DIG. 121, DIG. 122, DIG. 125, 103, 76

(56) References Cited

U.S. PATENT DOCUMENTS

| | | |
|---|---|---|
| 3,612,048 A | 10/1971 | Takaoka |
| 4,061,698 A | 12/1977 | Thornwald |
| 4,552,142 A | 11/1985 | Hoffman |
| 5,036,842 A | 8/1991 | van der Smissen |
| 5,245,996 A | 9/1993 | Manicom |
| 5,329,921 A | 7/1994 | Socaris |
| 5,471,979 A | 12/1995 | Psaros |
| 5,546,930 A * | 8/1996 | Wikefeldt ............... 128/201.13 |
| 5,590,644 A | 1/1997 | Rosenkoetter |
| 5,671,729 A | 9/1997 | Moll |
| 5,746,199 A | 5/1998 | Bayron |
| 5,829,428 A | 11/1998 | Walters |
| 6,095,135 A * | 8/2000 | Clawson et al. ........ 128/201.13 |
| 6,415,788 B1 * | 7/2002 | Clawson et al. ........ 128/201.13 |

FOREIGN PATENT DOCUMENTS

EP 0972534 1/2000

* cited by examiner

*Primary Examiner*—Weilun Lo
*Assistant Examiner*—Mital Patel
(74) *Attorney, Agent, or Firm*—August E. Roehrig, Jr.; Hancock & Estabrook, LLP

(57) ABSTRACT

A HME bypass system including a manually actuated bypass valve which is coupled into a respiratory air circuit, preferably upstream of the HME, to permit inspiratory air to be selectively passed through the HME, or to bypass the HME, depending upon the treatment desired by the healthcare provider.

10 Claims, 5 Drawing Sheets

HME BYPASS SYSTEM

BACKGROUND OF THE INVENTION

1. Field of the Invention

This invention relates in general to respiratory therapy devices and, in particular, to a single patient use bypass for allowing a patient to receive aerosol delivery of medication by selectively bypassing a heat and moisture exchanger, an HME, positioned in a ventilator circuit without removing the HME from the ventilating circuit.

More specifically, but without restriction to the particular embodiment and/or use which is shown and described herein for purposes of illustration, this invention relates to a humidifying filter bypass which permits the introduction of medication from a metered dose inhaler (MDI) or nebulizer into a ventilator circuit containing an HME without necessitating the removal of the HME from the circuit.

2. Description of Related Art

As is known to those in the respiratory care field, HME's are humidifying filters which are frequently used in medical procedures, for example in ventilator circuits such as when intubating patients, to prevent deterioration of respiratory functions. These devices capture heat and moisture on expiration, and return it to the patient on inspiration. In certain of such usages it is also necessary to administer medication to the patient in the form of a mist or fine spray which is inhaled by the patient.

To this end it is preferable that the medication be administered to the patient without passing through the HME for more effective administration. Accordingly, heretofore the procedure has been to physically remove the HME from the respiratory circuit during the administration of the medication, and then to re-install the HME into the circuit after the medication has been administered. While such a procedure is effective in the administration of the medication, the procedure is time consuming and can result in the introduction of undesired contaminants into the respiratory circuit as a result of the removal and reinstallation of the HME whenever the patient is required to be medicated. Accordingly, it would be highly beneficial and much more efficient if such medication could be administered to the patient without necessitating that the HME first be removed from the circuit and then re-installed after administration.

The present invention provides such a device through the use of a manually actuated bypass valve which is coupled into a respiratory air circuit, preferably upstream of the HME, to permit inspiratory air to be selectively passed through the HME, or to bypass the HME, depending upon the treatment desired by the healthcare provider. In this manner medication from an MDI or nebulizer can be conveniently administered to a patient through the circuit without the removal and reinsertion of the HME into the circuit, or the HME can continue to function uninterrupted.

SUMMARY OF THE INVENTION

It is an object of this invention to improve the delivery of aerosol medications in respiratory care circuits.

Another object of this invention is to provide a single patient use HME bypass for a ventilator circuit.

Still another object of this invention is to provide a manually actuable bypass valve for a ventilator circuit to selectively direct inspiratory air through an HME or to bypass the HME as desired.

Yet another object of this invention is to provide a single patient use HME bypass to selectively couple an HME into a ventilator circuit or to selectively bypass the HME when administering aerosol medication.

These and other objects are attained in accordance with the present invention wherein there is provided an HME bypass for use in respiratory therapy for selectively passing air through the HME or selectively bypassing the HME as determined by the healthcare provider.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein.

This and additional embodiments of the invention may now be better understood by referring to the following detailed description of the invention wherein the illustrated embodiment is described.

DETAILED DESCRIPTION OF THE INVENTION

Throughout this description, the preferred embodiment and examples shown should be considered as exemplars, rather than limitations on the apparatus and methods of the present invention.

Figure 1:
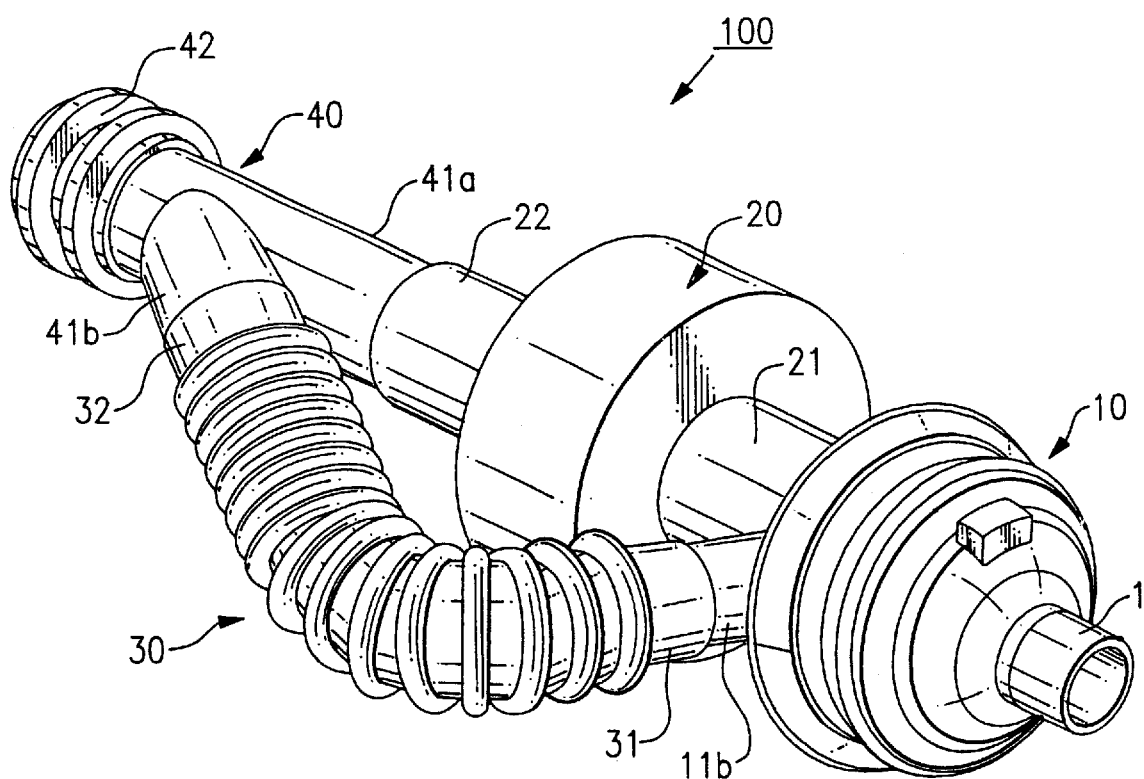
FIG. 1 is a frontal perspective view of the HME bypass system.
Figure 2:
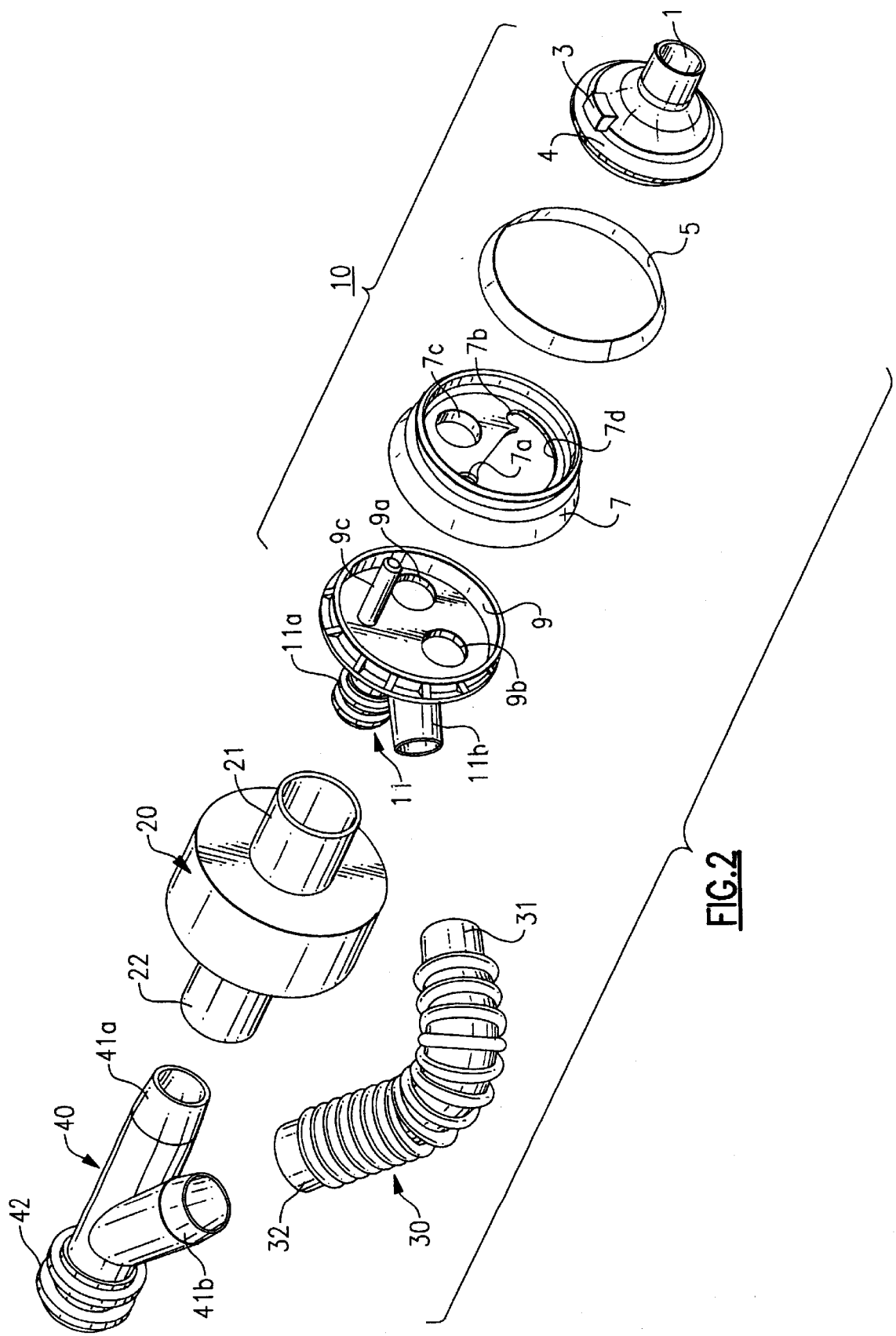
FIG. 2 is an exploded view of the HME bypass system to better illustrate the parts of the device and the components thereof.

Referring now to the drawings, there is shown in FIGS. 1 and 2, an HME bypass system 100 for selectively controlling the use or bypassing of a heat and moisture exchanger (HME) 20 in a breathing or respiratory circuit such as a ventilator circuit. As is known to those skilled in the art, a ventilator circuit is used to assist or facilitate a patient's breathing, such as in post surgical procedures, and to this end may employ an HME to capture heat and moisture upon the patient's expiration of air, and return it to the patient upon inspiration, thereby preventing deterioration of respiratory functions. HME's are available from a number of medical supply houses, and are generally of different sizes. However, all HME's have coupling portions 21 and 22 of a size, preferably 22 mm. and 15 mm., such that they can be connected into an air-flow circuit, such as into the tubing used in a ventilator circuit. The HME bypass system 100, couples the HME 20 into the air-flow circuit and provides a bypass to permit air flow around the HME, when desired, under the control of a manually actuable air-flow control valve 10, preferably positioned in the air-flow circuit upstream of the HME 20.

The air-flow control valve 10 includes a "Y" shaped coupling forming a discharge outlet 11 through which air flow is passed either to the HME 20, through a discharge outlet 11a, or when it is desired to bypass the HME 20, through a discharge outlet 11b. The air flow is thereafter passed through the remainder of the air-flow circuit. Preferably a flexible HME bypass air-flow tube 30 is coupled at an inlet end 31 to the air-flow control valve discharge outlet 11b, and extends a length sufficient to bypass the HME 20. A discharge end 32 of the air-flow tube 30 is coupled to a bypass inlet 41b of a second "Y" shaped coupling 40 forming an inlet to return the bypassed air to the air-flow circuit. A second inlet 41a of the "Y" shaped coupling inlet 40 is connected to the outlet 22 of the HME 20 to provide an inlet to receive air passed through the HME to couple the air passed therethrough into the air-flow circuit. A discharge outlet 42 is formed on the downstream end of the second "Y" shaped coupling 40 to connect the HME bypass system 100 into the air-flow circuit.

Figure 3:
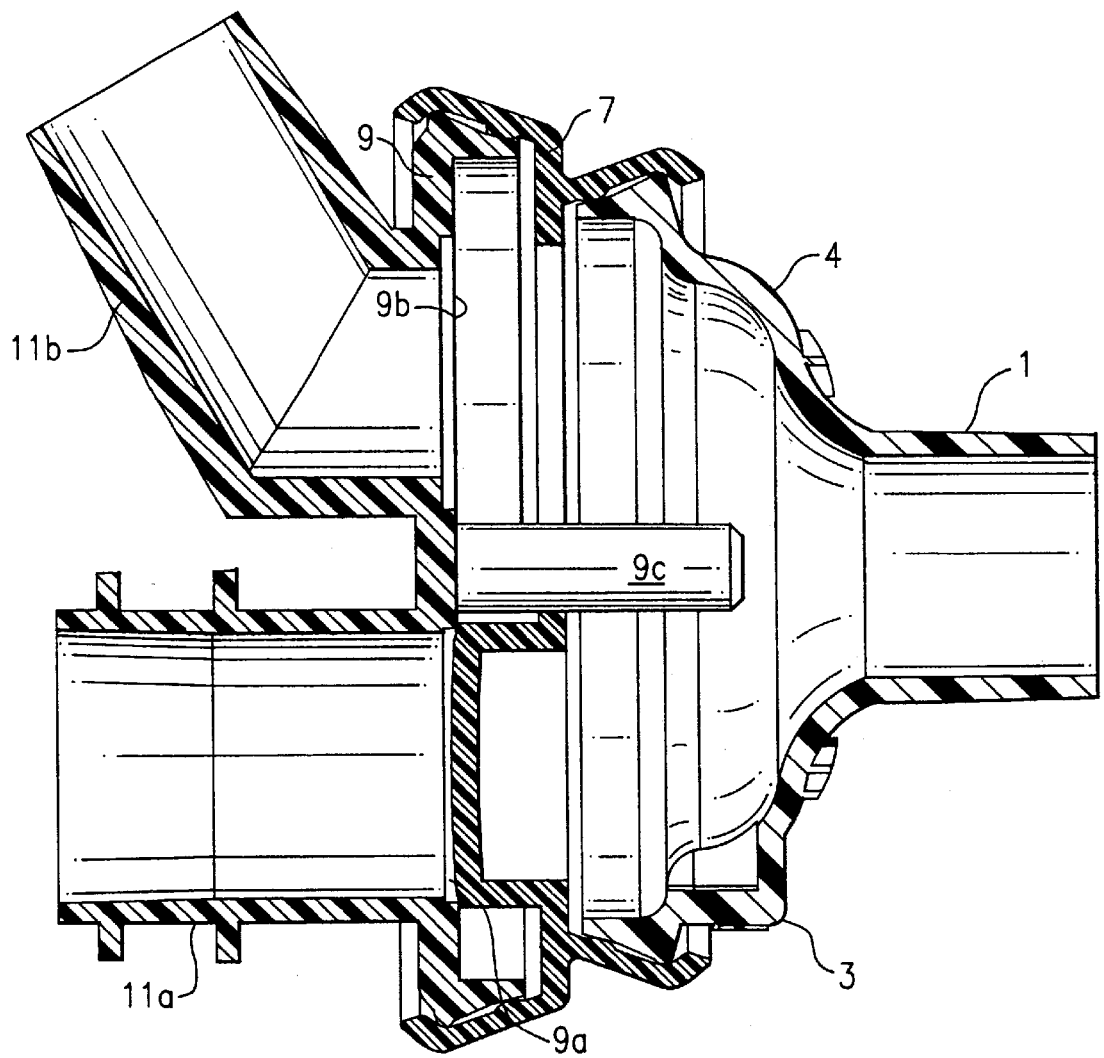
FIG. 3 is an enlarged cross sectional view of a manually actuable valve used in the invention to better illustrate the structure for selectively bypassing the HME.

Referring now to FIGS. 2 and 3, the air-flow control valve 10 is a manually actuable two-position valve for discharging air received through an inlet port or opening 1 into either the HME 20, through the control valve discharge outlet 11a, or the HME bypass, through the control valve discharge outlet 11b. To this end the control valve is formed with a circular-shaped base 9 having formed therethrough a pair of openings 9a and 9b which are aligned, respectively, to pass air through the discharge outlets 11a and 11b. The opening and closure of the two openings 9a and 9b is effected by the rotational movement of a control plate 7 which is rotatably supported in sealing engagement with the base 9 to mutually exclusively selectively align an aperture 7c formed in the control plate 7 with the openings 9a and 9b formed in the valve base 9. A stop pin 9c is carried by the valve base 9 and extends outwardly therefrom to pass through a motion limiting opening 7d formed in the control plate 7. The stop pin 9c limits the rotational movement of the control plate 7 between stop positions 7a and 7b, whereat the post 9c will become engaged with one of the stop positions 7a or 7b to align the aperture 7c with one of the openings 9a or 9b, respectively. A decorative ring 5 and cover 4 connect the portions of the air-flow valve 10 together, and an indicator 3, carried on the cover 4, provides visual and tactile indicia in combination with the decorative ring 5 as to the alignment of the aperture 7c with the openings 9a and 9b in the valve base 9. In this manner it may be determined through the indicator 3 if the air-flow control valve 10 is positioned to pass air flow through the HME 20 or to pass the air flow through the HME bypass tube 30.

Figure 4:
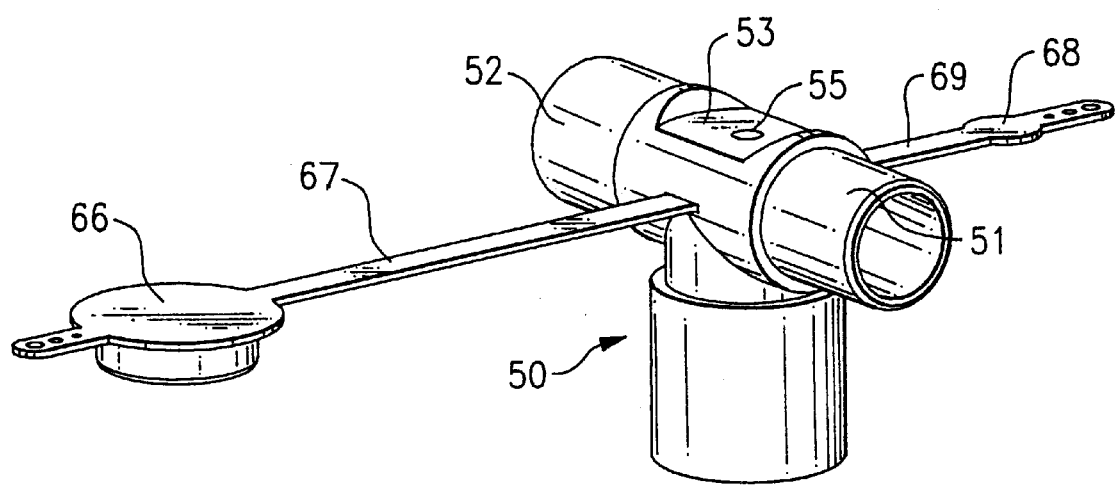
FIG. 4 is a frontal perspective view of an adapter than can be included in the circuit to facilitate the introduction of aerosol medication.
Figure 5:
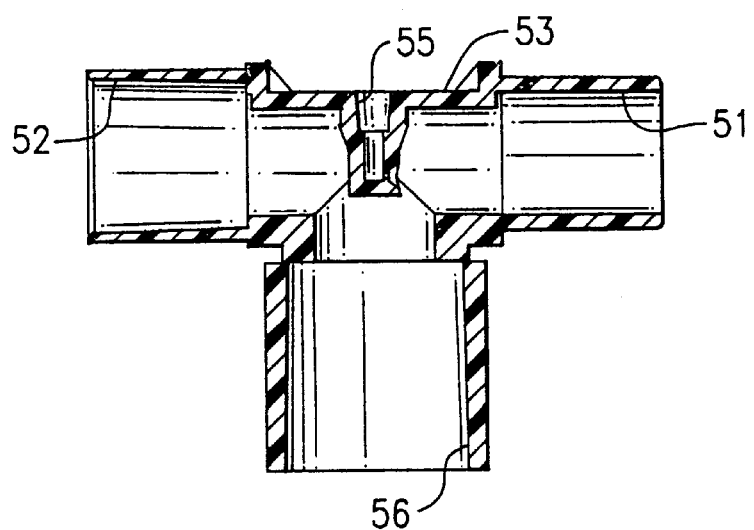
FIG. 5 is an enlarged cross sectional view of the adapter illustrated in FIG. 4 to better illustrate the internal construction thereof.
Figure 6:
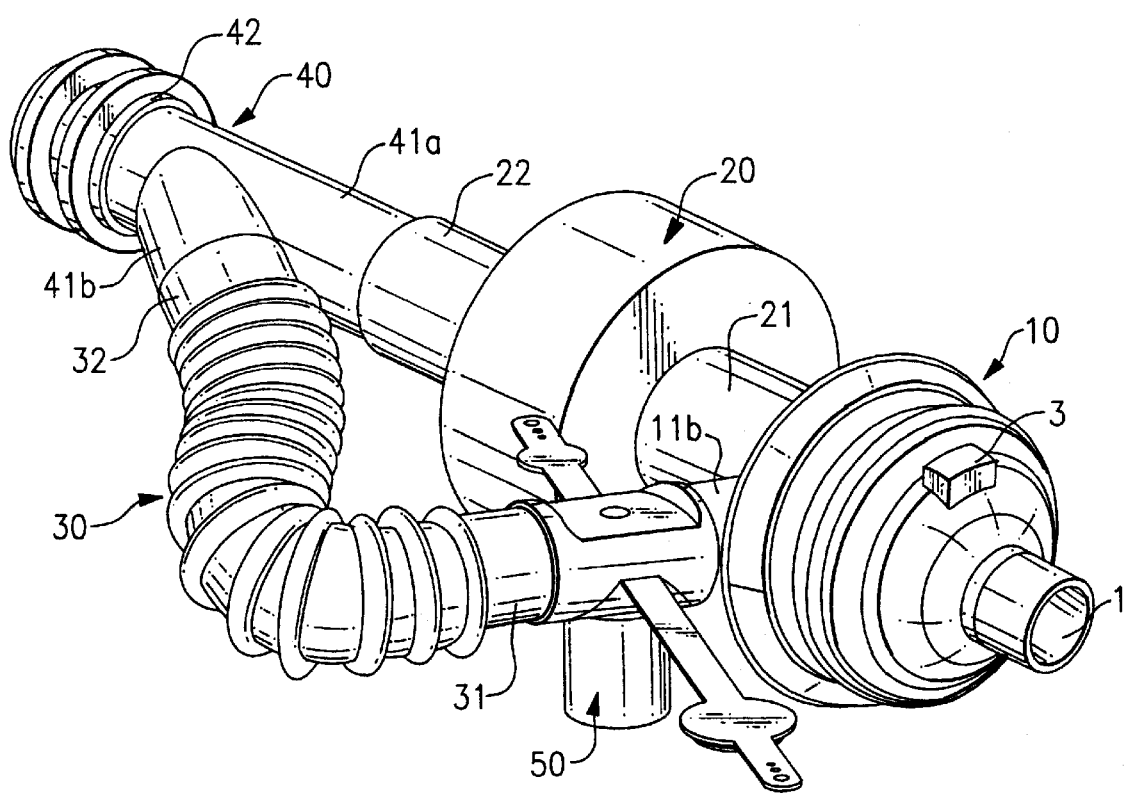
FIG. 6 is a frontal perspective view of the adapter illustrated in FIG. 4 inserted into the circuit of the apparatus illustrated in FIG. 1.

Referring now to FIGS. 4–6, there is illustrated a medication coupling 50 for connection into the HME bypass system 100, and the coupling 50 connected to the discharge outlet 11b of the air-flow control valve 10 to facilitate the use of a pressurized medication dispensing cannister such as the type used with a metered dose inhaler (MDI) or a nebulizer with the HME bypass tube 30 to conveniently introduce medications into the air-flow circuit. The medication coupling 50 includes an inlet 51 sized for connection to the discharge outlet 11b of the air-flow control valve 10, and an outlet 52 sized for connection to the inlet 31 of the HME bypass tube 30. An upper flat or planar portion 53 is formed with an aperture or medication port 55 of a size and type for receiving therein the discharge outlet of a pressurized medication dispensing canister (not shown) of the type used with an MDI to provide an opening through which such medication can be dispensed through the HME bypass tube 30 into the air-flow circuit. When a pressurized medication dispenser canister is used to dispense medication into the HME bypass tube 30, a closure cap 66, secured to the medication coupling 50 by a tether strap 67, is applied to an opening 56 on the side of the medication coupling 50 opposite to the aperture or port 53 to form a closure thereof so that the air flow through the medication coupling is from the inlet 51 through the outlet 52 to carry the medication dispensed into the medication coupling through the HME bypass tube 30.

The opening 56 in the medication coupling 50 is sized to receive and be connected to a standard nebulizer (not shown), so that medication which is desired to be introduced into the air flow by the use of a nebulizer can be conveniently administered. To this end a second closure 68, connected to the medication coupling 50 by a second tether 69, is applied to the aperture 55 and/or the planar portion 53 to close the opening so that the air flow through the medication coupling 50 is from the inlet 51 to through the outlet 52 to carry the medication through the HME bypass tube. While the medication coupling 50 is illustrated as being connected into the HME bypass system 100 at the discharge outlet 11b of the air-flow control valve 10, it is to be understood that the medication coupling can be connected to the inlet 1 of the air-flow control valve 10 if desired.

While this invention has been described in the specification and illustrated in the drawings with reference to preferred embodiments, the structures of which have been disclosed herein, it will be understood by those skilled in the art to which this invention pertains that various changes may be made, and equivalents may be substituted for elements of the invention without departing from the scope of the claims. Therefore, it is intended that the invention not be limited to the particular embodiments disclosed in the specification and shown in the drawings as the best mode presently known by the inventors for carrying out this invention, nor confined to the details set forth, but that the invention will include all embodiments, modifications and changes as may come within the scope of the following claims:

It is claimed:

1. An HME bypass for use in a breathing circuit to bypass breathing circuit air flow around an HME coupled into the breathing circuit comprising:

an air flow control valve adapted to be coupled into a breathing circuit for receiving breathing circuit air flow and having an inlet for connection to a source of breathing circuit air flow and at least a first air flow discharge outlet and a second air flow discharge outlet mutually exclusively connectable to the breathing circuit air flow received by said control valve through said inlet;

said first control valve discharge outlet connectable to an inlet of an HME for discharging the breathing circuit air flow received thereby through the HME to be passed through the breathing circuit;

said second control valve discharge outlet connectable to an inlet of an HME air flow bypass conduit for discharging the breathing circuit air flow received thereby in a path of movement bypassing the HME to the breathing circuit;

an HME air flow bypass conduit having an inlet for receiving breathing circuit air flow from said second air flow control valve discharge outlet and an outlet for passing breathing circuit air flow;

an air flow connector having at least a first inlet connectable to an outlet of an HME for coupling breathing circuit air flow from the HME and a second inlet connectable to said HME air flow bypass conduit outlet for coupling breathing circuit air flow from said HME air flow bypass conduit; and said air flow control valve actuable between a first position wherein said breathing circuit air flow is only coupled to the HME and a second position wherein said breathing circuit air flow is only coupled to said HME air flow bypass conduit.

2. The HME bypass of claim 1 further including a medication coupling for connection into the HME air flow bypass conduit:

said medication coupling including an air flow inlet adapted to be connected to said control valve second discharge outlet, and an air flow outlet adapted to be connected to said HME air flow bypass conduit inlet;

said medication coupling further including a first aperture formed therein for receiving a discharge outlet of a pressurized medication dispenser for discharging medication therethrough into the breathing circuit air flow.

3. The HME bypass of claim 2 further including a second aperture formed in said medication coupling for receiving a discharge outlet of a nebulizer for discharging medication therethrough into the breathing circuit air flow.

4. The HME bypass of claim 3 further including a closure for said first and second apertures to prevent the introduction of air flow therethrough when a pressurized medication dispenser or nebulizer discharge outlet is not engaged therewith to discharge medication into the breathing circuit air flow.

5. The HME bypass of claim 1 wherein said air flow control valve is manually actuable to mutually exclusively couple the breathing circuit air flow received from said control valve inlet to said first and said second control valve discharge outlets.

6. A breathing circuit apparatus including an HME and an HME bypass for use in a breathing circuit to bypass breathing circuit air flow around the HME into the remainder of the breathing circuit comprising:

an air flow control valve coupled into a first portion of a breathing circuit and having an inlet for connection to a source of breathing circuit air flow and at least a first discharge outlet connected to an HME inlet and a second discharge outlet connected to an HME bypass conduit inlet;

an HME having an inlet for receiving breathing circuit air flow from said air flow control valve first discharge outlet and an outlet for passing the breathing circuit air flow received therefrom to a remainder portion of said breathing circuit;

an HME air flow bypass conduit having an inlet for receiving breathing circuit air flow from said air flow control valve second discharge outlet and an outlet for passing breathing circuit air flow received therefrom to said remainder portion of said breathing circuit;

an air flow connector having at least a first inlet connected to said HME outlet for coupling breathing circuit air flow from said HME to said remainder portion of said breathing circuit and a second inlet connected to said HME air flow bypass conduit outlet for coupling breathing circuit air flow from said HME air flow bypass conduit to said remainder portion of said breathing circuit; and said air flow control valve actuable between a first position wherein said breathing circuit air flow is coupled only to said HME and a second position wherein said breathing circuit air flow is coupled only to said HME air flow bypass conduit.

7. The breathing circuit apparatus of claim 6 wherein said air flow control valve is manually actuable to mutually exclusively couple the breathing circuit air flow received from said control valve inlet to said first and said second control valve discharge outlets.

8. The breathing circuit apparatus of claim 6 further including a medication coupling for connection into said HME air flow bypass conduit:

said medication coupling including an air flow inlet adapted to be connected to said control valve second discharge outlet, and an air flow outlet adapted to be connected to said HME air flow bypass conduit inlet;

said medication coupling further including a first aperture formed therein for receiving a discharge outlet of a pressurized medication dispenser for discharging medication therethrough into the breathing circuit air flow.

9. The breathing circuit apparatus of claim 8 further including a second aperture formed in said medication coupling for receiving a discharge outlet of a nebulizer for discharging medication therethrough into the breathing circuit air flow.

10. The breathing circuit apparatus of claim 9 further including a closure for said first and second apertures to prevent the introduction of air flow therethrough when a pressurized medication dispenser or nebulizer discharge outlet is not engaged therewith to discharge medication into the breathing circuit air flow.

* * * * *